United States Patent
Kawasaki et al.

(10) Patent No.: US 7,422,208 B2
(45) Date of Patent: Sep. 9, 2008

(54) SHEET MATERIAL INFORMATION-DETECTING APPARATUS

(75) Inventors: Takehiko Kawasaki, Tokyo (JP); Norio Kaneko, Atsugi (JP); Naoaki Maruyama, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 376 days.

(21) Appl. No.: 10/538,267

(22) PCT Filed: Feb. 20, 2004

(86) PCT No.: PCT/JP2004/002015

§ 371 (c)(1),
(2), (4) Date: Jun. 10, 2005

(87) PCT Pub. No.: WO2004/073990

PCT Pub. Date: Sep. 2, 2004

(65) Prior Publication Data

US 2006/0022400 A1  Feb. 2, 2006

(30) Foreign Application Priority Data

Feb. 20, 2003 (JP) ............................. 2003-043271
Feb. 18, 2004 (JP) ............................. 2004-041999

(51) Int. Cl.
*B65H 5/00* (2006.01)
(52) U.S. Cl. .......................... 271/225; 347/43; 271/226
(58) Field of Classification Search ................. 271/227, 271/185, 225, 226
See application file for complete search history.

(56) References Cited

U.S. PATENT DOCUMENTS

| 3,470,734 | A | * | 10/1969 | Agdur et al. ................. 73/32 A |
| 5,104,488 | A | * | 4/1992 | Chase ......................... 162/198 |
| 5,123,284 | A | | 6/1992 | Edinburgh et al. |
| 5,475,233 | A | | 12/1995 | Fukuoka et al. |
| 5,774,146 | A | | 6/1998 | Mizutani |
| 5,852,499 | A | * | 12/1998 | Tomita et al. ................ 356/429 |
| 6,291,829 | B1 | | 9/2001 | Allen et al. |
| 2002/0039495 | A1 | | 4/2002 | Metzler |
| 2002/0181963 | A1 | | 12/2002 | Takeda |

OTHER PUBLICATIONS

U.S. Appl. No. 10/536,912, filed May 27, 2005, T. Kawasaki et al.
U.S. Appl. No. 11/144,647, filed Jun. 6, 2005, N. Kankeo et al.

* cited by examiner

*Primary Examiner*—Kaitlin S Joerger
(74) *Attorney, Agent, or Firm*—Fitzpatrick, Cella, Harper & Scinto

(57) ABSTRACT

A sheet material information-detecting apparatus is provided which is capable of detecting the type of a sheet material even if the sheet material is anisotropic. When recording paper sheet P is fed, feed rollers 1*a* and 1*b* are moved to narrow the nip of the rollers and front edge of recording paper sheet is pushed thereto to correct the oblique feed. Thereafter, external force is applied to recording paper sheet P by external force applying member 2. A signal based on the external force is detected by signal detecting means 3, and sheet material information-acquiring means 5 identify the type of the recording paper sheet. Owing to the oblique feed correction, the type of the sheet material can be identified precisely even if the sheet material is anisotropic.

13 Claims, 8 Drawing Sheets

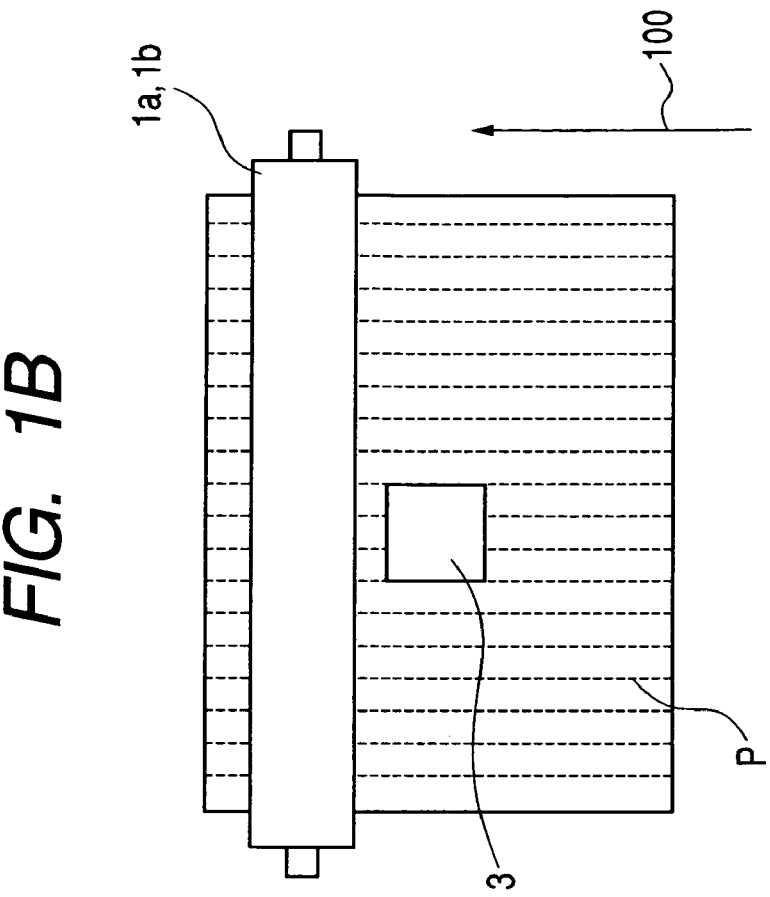
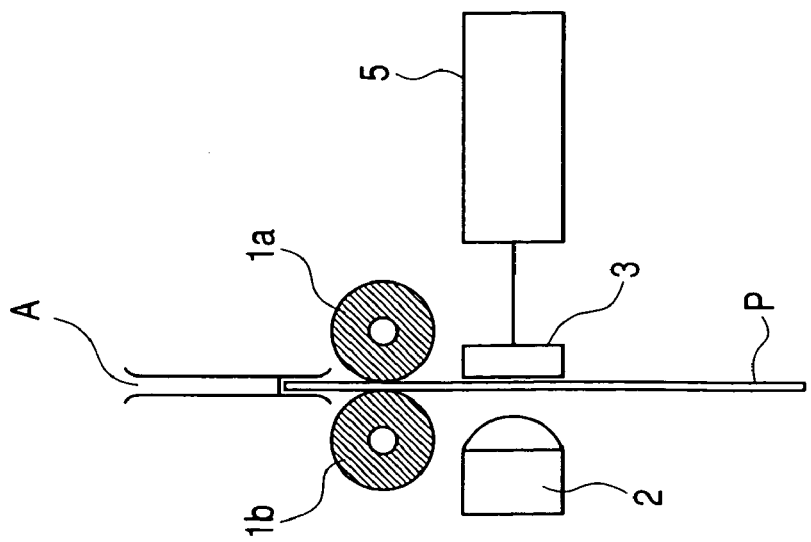

SHEET MATERIAL INFORMATION-DETECTING APPARATUS

TECHNICAL FIELD

The present invention relates to an apparatus for acquiring information on a sheet material.

BACKGROUND ART

In recent years, apparatuses for obtaining information on sheet materials are attracting attention. For instance, U.S. Pat. No. 6,291,829 discloses a device for identifying the type of recording paper sheet provided in an image-forming apparatus.

The sheet materials to be detected include anisotropic materials. U.S. Pat. No. 5,475,233 discloses a method for measuring orientation of fiber in anisotropic materials.

In identification of an anisotropic sheet material with a sheet material information-detecting apparatus by application of an external force, the detection result depends on the relative position of the sensor to the sheet material. Therefore, for detection of information on the sheet material fed successively to an image-forming apparatus, so-called oblique feed of the sheet should be prevented to obtain precise information. This is explained below specifically.

Paper sheets produced from wood pulp as the main source material, for instance, are widely used as recording sheets. The paper sheets have anisotropic characters owing to orientation of the fiber in a specific direction (machine direction) in the paper making process.

Such paper sheets, which are generally cut in machine direction and cross direction, are anisotropic in characteristics according to the sheet cutting directions as called "crosswise orientation" or "lengthwise orientation" based on the cutting ends, and the properties thereof differ depending on the orientation directions: the properties such as rigidity, distortion by force, elongation at break, Young's modulus, swelling and curling by water absorption, light reflectivity, surface roughness, and periodic structure.

The inventors of the present invention have studied on detection of information on sheet materials by application of external force onto sheet materials fed successively to an image-forming apparatus or the like. As the results, the inventors have found newly that, when a paper sheet having the aforementioned orientation comes to be fed with its orientation direction oblique to the sheet feed direction, the information on the sheet material is affected by the anisotropy. Such a problem arises also in coated paper sheets and resin films having orientation caused by the production process.

The present invention provides a sheet material information-detecting apparatus excellent in information detecting accuracy.

DISCLOSURE OF THE INVENTION

The present invention is made to solve the above problem.

According to an aspect of the present invention, there is provided a sheet material information-detecting apparatus comprising:

a sheet feeding means for feeding a sheet material;

a correcting means for correcting the position of the fed sheet material to bring the orientation direction of the constituting material of the sheet material to be in a prescribed direction relative to the feed direction of the sheet material;

an external force applying means for applying an external force to the sheet material in the corrected position; and an information-acquiring means for acquiring information corresponding to the stress caused by the applied external force in the sheet material.

According to another aspect of the present invention, there is provided a sheet material information-detecting apparatus comprising:

a sheet feeding means for feeding a sheet material;

a correcting means for correcting the position of the fed sheet material to bring the orientation direction of the constituting material of the sheet material to be in a prescribed direction relative to the feed direction of the sheet material;

an external force applying means for applying an external force to the sheet material in the corrected position;

a signal-detecting means for detecting signal from the sheet material; and an information-acquiring means for acquiring information on the stress caused by the applied external force corresponding to the sheet material.

According to still another aspect of the present invention, there is provided a sheet-material treating apparatus, comprising the aforementioned sheet material information-detecting apparatus, and a sheet material-treating assembly for treating the sheet material by utilizing the information obtained by the sheet information-detecting apparatus.

According to a further aspect of the present invention, there is provided a sheet material feeding unit comprising the aforementioned sheet material information-detecting apparatus, and a driving assembly for the sheet material feeding means.

According to a still further aspect of the present invention, there is provided a process for acquiring information on a sheet material, comprising the steps of:

correcting the position of a fed sheet material to bring the orientation direction of the constituting material of the sheet material to be in a prescribed direction relative to the feed direction of the sheet material;

applying an external force to the sheet material placed in the corrected position; and acquiring information corresponding to the stress caused by the applied external force in the sheet material.

BRIEF DESCRIPTION OF THE DRAWINGS

FIG. 1A illustrates an example of the structure of the sheet material information-detecting apparatus of the present invention. FIG. 1B is a plan view of the structure of FIG. 1.

BEST MODE FOR CARRYING OUT THE INVENTION

Figure 2:
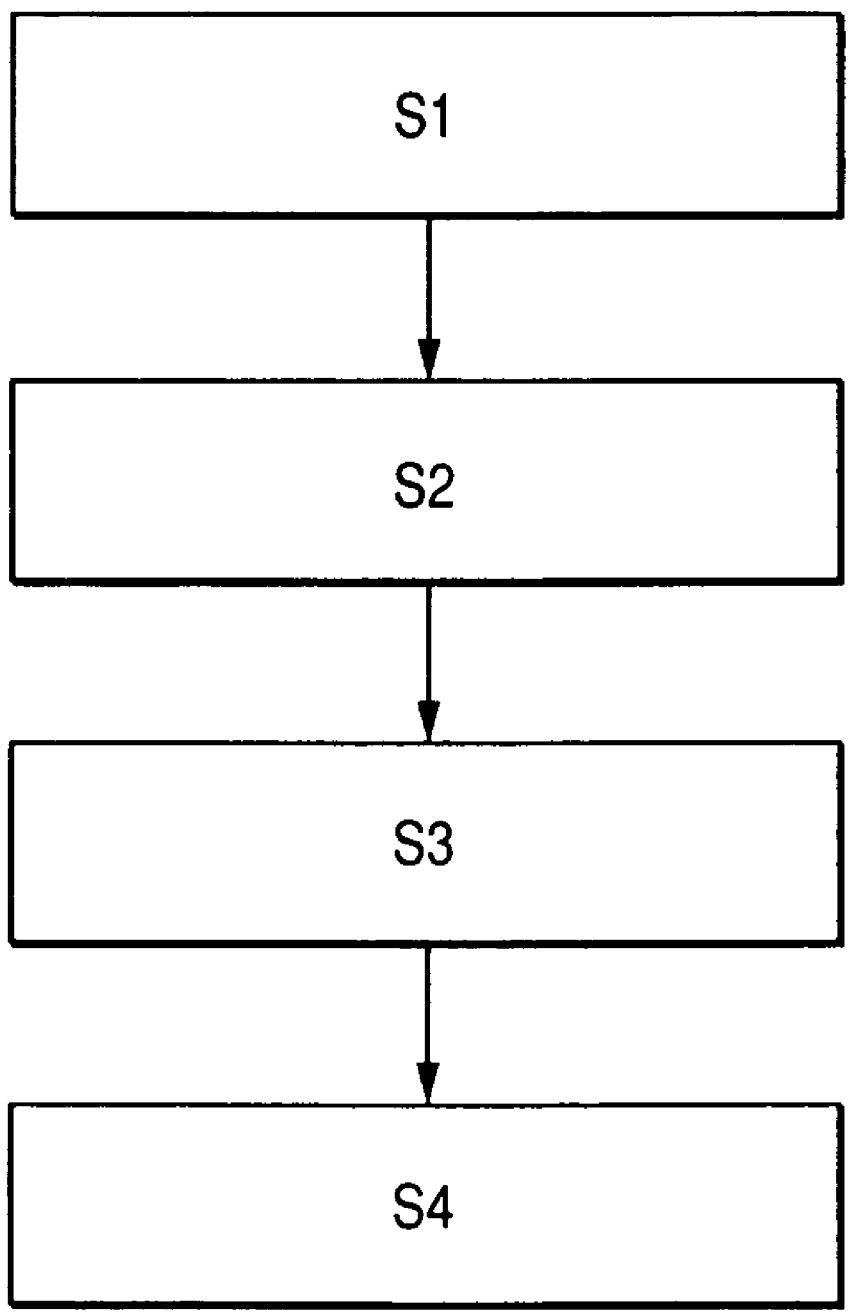
FIG. 2 is a flow chart for explaining the operation of the sheet material information-detecting apparatus of the present invention.

The sheet material information-detecting apparatus comprises a sheet material sensor for sensing interaction of an external force-applying means and a signal detecting means with the sheet material.

The sheet material sensor can sense the state or position of the sheet material.

The sheet material information-acquiring means can acquire the information on the sheet material by comparison of the detection results of the signal detecting means with a data.

The sheet material information-acquiring means can acquire the information on the sheet material by comparison of the results of detection of the signal detecting means with a data for directions of sheet material.

The external force includes a mechanical force. This mechanical force may be plural times of impacts at different collision velocity.

The external force includes vibrations having different frequency components.

The external force includes a wave.

The external force includes a light beam.

The sheet material information detection apparatus comprises a restricting member which restricts the region of displacement of the sheet material on application of the external force.

The embodiment of the present invention is explained by reference to FIGS. 1 to 3. In the figures, like reference characters indicate like parts or meanings.

As shown in FIG. 1, the sheet material information-detecting apparatus of the present invention comprises sheet material feeding means 1a and 1b for feeding a sheet material P along sheet material feeding path A, external force applying means 2 for applying an external force to fed sheet material P, and signal-detecting means 3 for detecting signal caused by the external force, and sheet material information-acquiring means 5: the information on sheet material P is obtained according to the detection results of the signal detecting means 3. An arrow 100 denotes the direction of feeding the sheet material.

The orientation of the sheet-constituting material, in the present invention, signifies fiber orientation caused in the paper making process for paper sheets, and molecule orientation caused by stretching for resin films.

The sheet material information-detecting apparatus of the present invention comprises an oblique feed correcting means for correcting the oblique introduction of the sheet material P through the sheet feed path (correction of the sheet feed direction), and applies an external force by the external force applying means after the correction of the oblique sheet introduction.

With the sheet material information-detecting apparatus of the present invention, sheet feeding means 1a and 1b feed a sheet material P, the oblique feed correcting means corrects the oblique introduction of sheet P (step S1 in FIG. 2), external force-applying means 2 applies the external force to sheet material P (step S2 in FIG. 2), signal-detecting means 3 detects the signal caused by the external force (step S3 in FIG. 2), and from the detection result (e.g., electric signal), the information on the sheet material is obtained (step S4 in FIG. 2).

An oblique feed correcting means, as an example, takes selectively either a first position to project into sheet feed path A or a second position to withdraw from sheet feed path A.

The correcting means corrects the oblique sheet introduction by taking the first position by pushing the front edge of sheet material P, and then allows the feed of sheet material P by taking the second position. Such an oblique feed correcting means is provided as a single-functional member for oblique feed correction, like a so-called shuttering member.

In another example, the oblique feed correcting member employs feeding rollers 1a and 1b, as shown in FIG. 1A, which corrects oblique feed by narrowing the nip and allows feed of sheet material P by widening the nip. In this example, the oblique feed is corrected by pushing the front edge of the sheet material against the roller nip, or the like. If necessary for the correction, feed driving force is further applied to control the angle of the sheet front edge.

Figure 3:
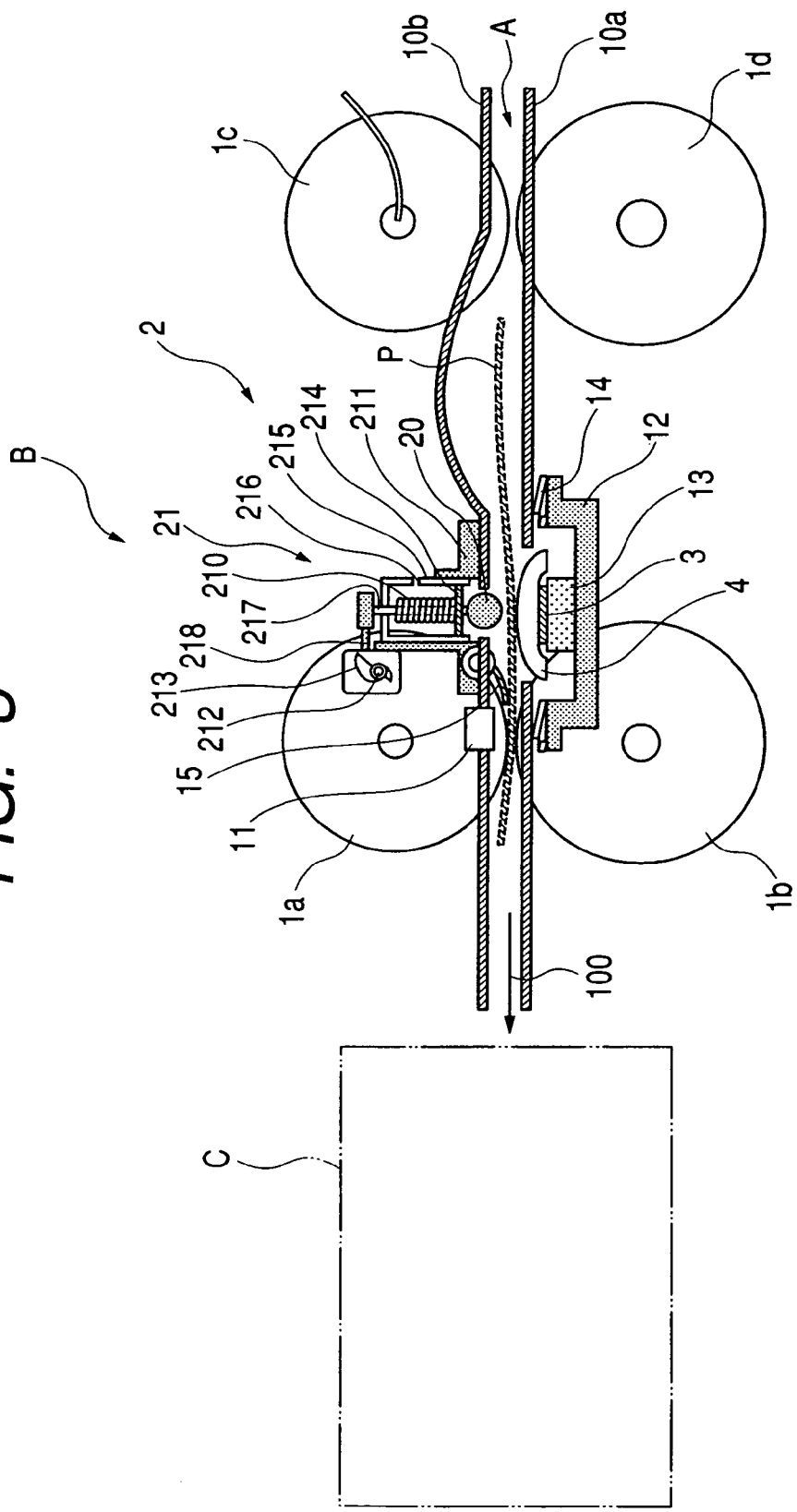
FIG. 3 is a sectional view illustrating an example of the structure of the sheet material information-detecting apparatus of the present invention.

Sheet material P can be corrected not only for the oblique feed within the plane of sheet material P by the oblique feed correcting means, but also for the position in the thickness direction of sheet material P by a sheet material displacing means (reference number 4 in FIG. 3). The external force is applied preferably by the aforementioned external force applying means 3 after the position correction by the sheet displacing means.

The sheet material information can be acquired manually based on the detection result derived by signal detecting means 3, or automatically by inputting the detection result by the signal detecting means 3 to the sheet material information-acquiring means (reference number 5 in FIG. 1A). Incidentally, the detection result transmitted from signal detecting means 3 may be utilized without processing, or after simple processing such as filtering, or after extraction of the characteristics such as voltage, cycle period, frequency component, differential, integral, attenuation, and peak number.

<Detection of Frequency Components of Detected Signals>

Naturally, the obtained one output waveform may be subjected to extraction of plural characters, and combination of the extracted characters may be utilized for the identification. Otherwise, one output signal may be branched into plural fractions and the respective branched signal fractions may be processed separately in different manners. For instance, the branched signal fractions are respectively subjected to filtering with different cutoff frequencies to extract different frequency components and obtain the intensity ratio.

The sheet material information-acquiring means 5 may be used to comparing the detected results obtained by signal-detecting means 3 with known data for acquiring the sheet material information. That is, the sheet material information-acquiring means 5 may be used by comparing the acquired character data with a memorized data table and to output information on the kind, type, state change, printed state, multiple sheet feed, and so forth of the sheet material. In the case where the signal from the sheet material varies depending on the environmental conditions, the sheet feeding state and so forth, plural data tables are prepared correspondingly as the reference standard for the judgment. When plural signal detecting means 3 are employed or plural times of signal detection is conducted by changing the external force application conditions, the data tables are provided correspondingly.

For discriminating an anisotropic sheet material, sheet material information-acquiring means may be made to acquire the sheet material information by comparing the detection results of the aforementioned signal-detecting means 3 with memorized data (data for orientation-directions of the sheet material). For example, data tables are provided for feeding a regular-sized sheet material (e.g., A4 size) in a longitudinal direction and in a cross direction (breadth direction). Since most of commercial sheet materials are classified into lengthwise oriented ones and crosswise oriented ones, the data tables are preferably prepared for the orientation directions. Further, the sheet material may be identified by utilizing combinedly other procedures (e.g., input of paper sheet type-numbers set artificially, and signals from a separately provided sensor). Furthermore, a logic circuit is preferably provided for judging from combination of plural detection results or plural judgment results.

The detected signal may be processed for subtracting the output signal in no sheet feeding state. The circuit for this signal processing can process signals by utilizing a first signal detected by the sensor on external force application without the pinched sheet material and a second signal detected by the sensor on external force application with the sheet pinched.

The "sheet material" in this Specification includes recording mediums such as plain paper sheets, glossy paper sheets, coated paper sheets, regenerated paper sheets, and OHP; and recorded document sheet materials.

The "sheet material information" in this Specification includes kind or type-numbers, densities, thicknesses, surface roughnesses, state changes, and printed states of the sheet materials; occurrence of overlapping sheet feeding, overlapping sheet numbers, unused remaining sheet numbers, presence of the sheet material, and overlapping position of the sheet materials.

The application of the external force by external force-applying means 2 should be conducted after correction of the oblique feed. The setting position of external force-applying means 2 is not limited to a downstream side of the oblique feed correcting means (downstream side along the sheet feed direction), but may be an upstream side of the oblique feed-correcting means. With external force-applying means 2 set at the downstream side of the oblique feed-correcting means, the external force may be applied to sheet material P being in contact with the oblique feed-correcting means, or to sheet material P having passed through the oblique feed-correcting means. On the other hand, with external force-applying means 2 placed at the upstream side of the oblique feed-correcting means, the external force may be applied to sheet material P having been corrected for oblique feed by contact with the oblique feed-correcting means. Since the detected information (sheet material information) is used in a later step for controlling the sheet material-treating assembly (symbol C in FIG. 3), the detection of information should be conducted in a possible shortest time after the oblique feed correction. Therefore, external force-applying means 2 is placed preferably at the upstream side of the oblique feed-correcting means, or very close to the oblique feed-correcting means at the downstream side. The distance between external force-applying means 2 and the oblique feed-correcting means is decided in consideration of the size or other properties of the sheet material to be detected.

This external force-applying means 2 may be the ones which apply external force by bringing an external force-applying member (reference number 20 in FIG. 3) into contact with the sheet material, or the ones which blows a gas like air. External force applying member 20 is preferably driven by a driving source (reference number 21 in FIG. 3).

The external force in the present invention includes electricity, magnetism, heat, thermal expansion/contraction of a gas or the like, optical beams such as laser beams, electromagnetic waves, sonic waves, vibration, and mechanical force, but is not limited thereto. The external force may be applied as impact, or as vibration.

The driving source for application of the impact includes the ones which hold external force applying member 20 above sheet material P and allow the member 20 to fall onto sheet material P, and the ones which allow external force applying means 20 to collide against sheet P by a mechanical or electromagnetic energy (e.g., mechanical means like a spring, electromagnetic means like a solenoid or a voice coil). In preferred examples, a rotational force of a motor or a roller of sheet feeding system is changed in direction or strength by a conversion mechanism such as gear and cam. Such mechanisms are preferred in view of the stability.

The driving source for application of vibration includes vibrating means for vibrating external force applying member 20 (e.g., piezoelectric actuators, electrostatic actuators, and electromagnetic sound generators).

For applying the impact force, external force applying member 20 may be allowed to collide against sheet material P. Otherwise, external force applying member 20 kept in contact with sheet material P may be impacted. In this case, the application of external force is conducted with the member 20 kept in contact with sheet material P. External force applying member 20 may be brought into contact with sheet material P only at the time of external force application, or may be kept in contact with sheet material P before the external-force application. In the former case, when the external force applying means and the signal detecting means are placed in opposition, the distance between the external force applying means and the signal detecting means comes to be changed (shortened). Since application of external force by the external force applying means can deform the sheet material slightly (formation of a hollow or the like), the external force is applied preferably at the edge or end of the sheet material.

The external force may be applied to sheet material P in a feeding state, or may be applied to sheet material P in a temporarily stopping state. The external force application to sheet material P in a feeding state has an advantage of ease of detection of the surface state of the face of the sheet material (at the external force application side), whereas the external force application to sheet material P in a stopping state has an advantage of preciseness of detection owing to the absence of noise caused by sheet feeding. The state of the sheet material in the detection may be selected as necessary.

The external force includes several kinds of forces as mentioned above. Only one kind of external force may be employed, or plural kinds of external forces may be employed. When one kind of external force is employed, one external force application may be conducted for obtaining the information, or plural times of external force application may be conducted for obtaining the information. By the plural times of external force application (one kind of external force plural times, or plural kinds of external forces), plural data can be obtained, improving the judgment accuracy. The plural times of external force application may be conducted with one external force applying member, or with plural external force applying members. In the plural times of external force application, the strength of the external force (impact strength, or vibration intensity) may be kept constant, or may be varied. In the plural times of external force application, a subsequent external force is preferably applied after the shake of the sheet material by the preceding external force has come to attenuate sufficiently or become lower than a prescribed level.

Further, preferred mode of plural times of external force application includes plural times of impacting at different collision velocity, and vibration in different frequency components. By such external force application, the viscoelasticities of polymeric sheet materials can be reflected efficiently on the output signal, which enables output of more detailed information of the sheet materials. Furthermore, by plural times of external force application, plural pieces of information can be outputted from signal detection means 3.

In order to detect the information with high precision, a member is provided in opposition to external force applying member 20 with interposition of sheet material P to stop the external force (the member hereinafter referred to as an "external force stopping member"). With sheet displacing means 4 placed in opposition to external force applying member 20, the sheet displacing means 4 is allowed to function as the external force stopping member (to stop the external force by this displacing means without providing additional external force stopping member). When displacing means 4 is not opposed to external force applying member 20, an external force stopping member is provided in opposition to external force applying member 20. The sheet contact face of such an external force stopping member may be a flat plane or a curved plane. On the external force stopping member, a recess may be formed at the position opposing through the sheet material to the tip of external force applying member 20 to avoid concentration of the external force to one point for lengthening the life of the element. The recess is preferably formed since the absorption of the external force by the sheet material by being deformed toward the recess by the external force can be detected.

The aforementioned sheet displacing means 4 may be of any construction, provided that it is capable of displacing the sheet material, being exemplified by the ones which displace the sheet material with interposition of a cushioning layer like air, and the ones which a displacing member is allowed to protrude into the sheet material feed path to come into contact with the sheet material and to displace it. When the sheet displacing means is employed as the external force stopping member, the sheet displacing means should be of the latter type.

This sheet displacing means may be utilized for defining the position of the sheet materials: the position relative to signal detecting means 3 (interval between sheet material P and signal detecting means 3); the position relative to external force applying member 20 (interval between sheet material P and external force applying member 20); or the position relative to the external force stopping member (interval between sheet material P and external force stopping member). Incidentally, by defining the position of the sheet material relative to the external force stopping member, the bending of the sheet material caused by the external force application can be made constant to enable stable detection independently of the applied external force. More preferably, this sheet displacing means brings sheet material P into contact with the external force stopping member. For such control, the external force stopping member is placed to push the sheet material, or the sheet displacing means is constituted to displace the sheet material in the direction to push the external force stopping member.

<Restricting Member>

Figure 5:
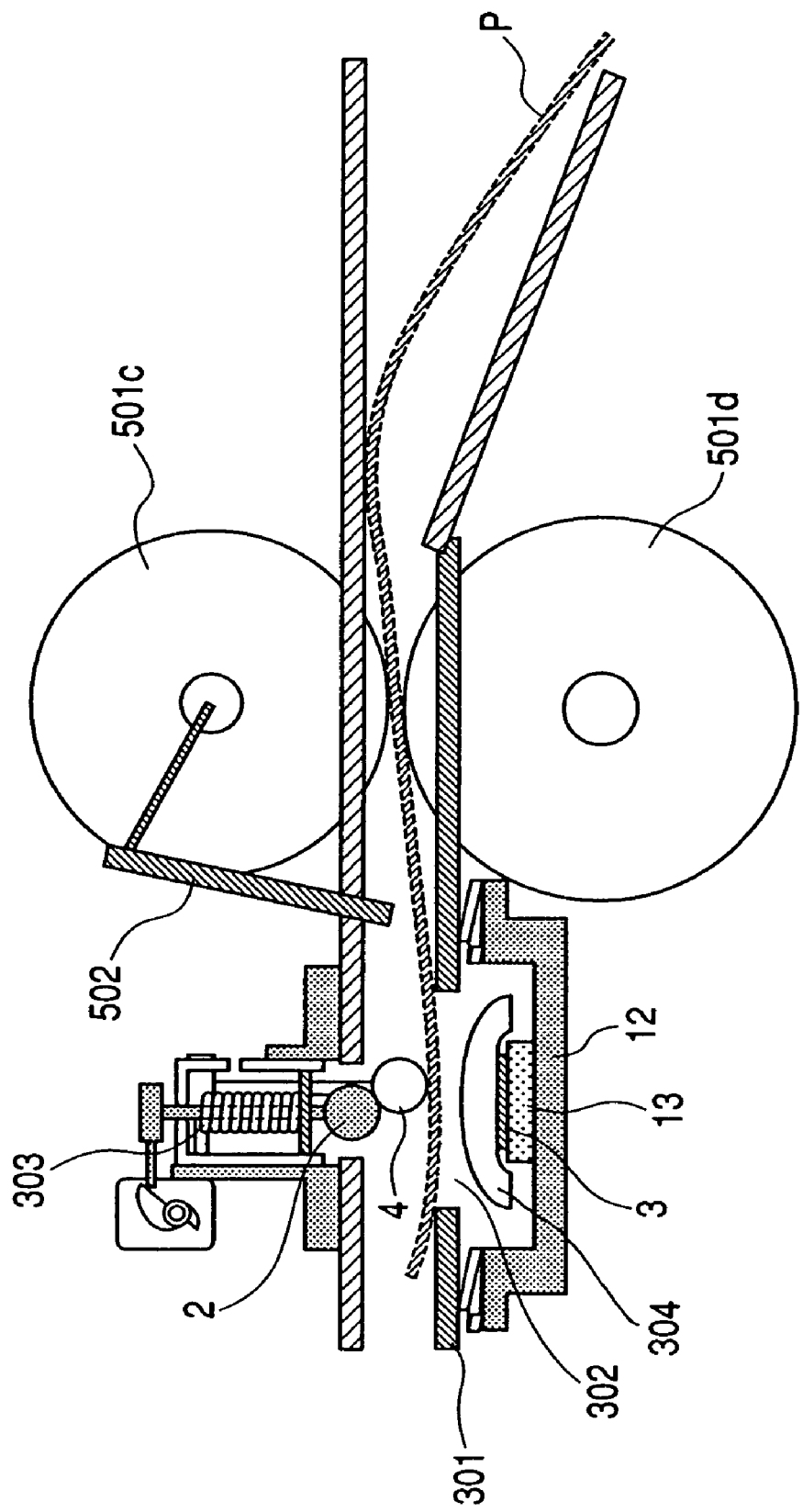
FIG. 5 illustrates an example of the sheet feeding unit of the present invention.
Figure 6:
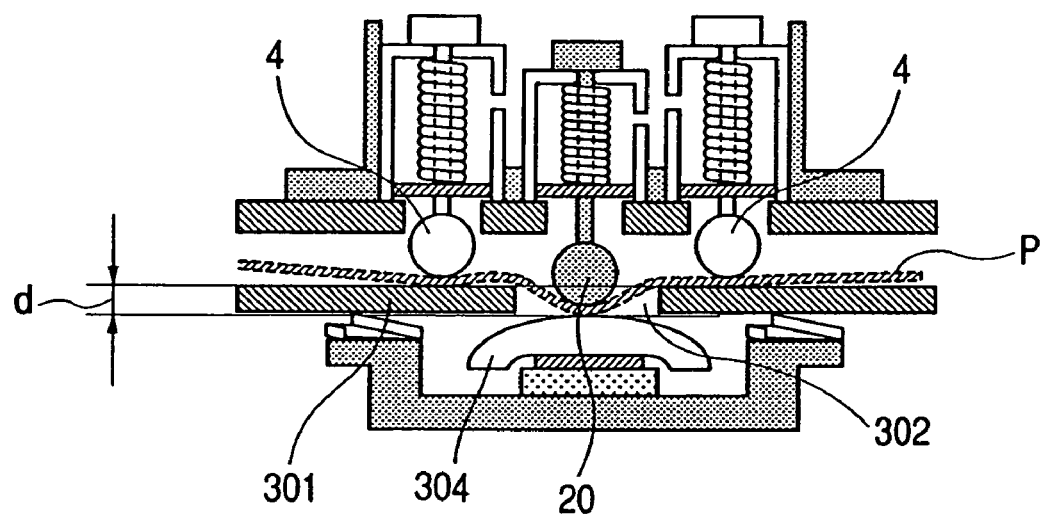
FIG. 6 illustrates the operation of the sheet material information detection employing a restricting member according to the present invention.
Figure 7:
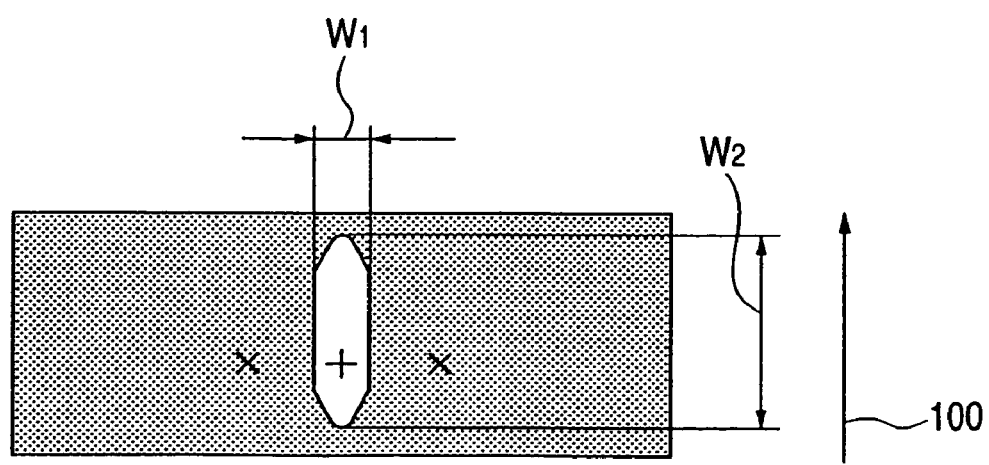
FIG. 7 illustrates an example of the shape of the restricting member (plan view).
Figure 8:
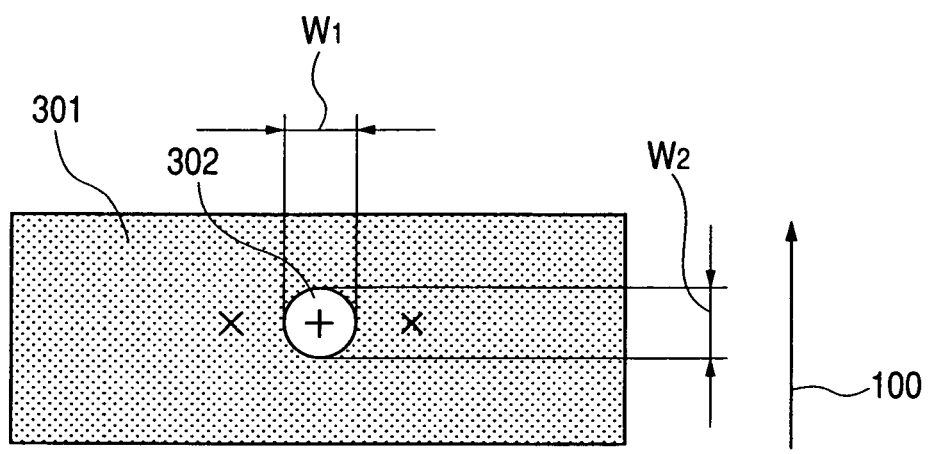
FIG. 8 illustrates an example of the shape of the restricting member (plan view).
Figure 9:
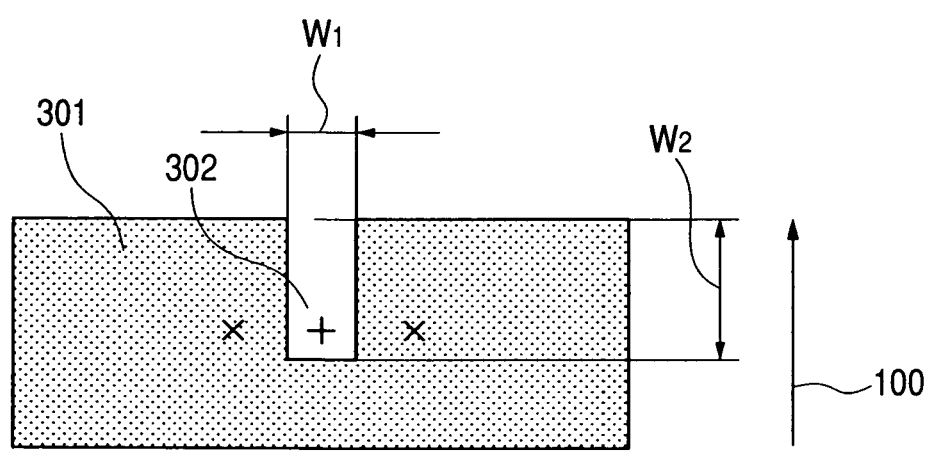
FIG. 9 illustrates an example of the shape of the restricting member (plan view).

A restricting member is preferably provided which restricts the region of displacement of the sheet material on application of the external force. FIG. 5 shows an example of the sheet material information-detecting apparatus employing a restriction member of the present invention. FIG. 6 illustrates the operation of the sheet material information detection employing a restricting member. FIGS. 7, 8 and 9 illustrate examples of the restricting member.

In FIG. 5, fed sheet material P is corrected for oblique feed by an oblique-feed correcting means, and is displaced to a prescribed position by sheet displacing means 4. By this displacement, the sheet material is preferably pushed to restricting member 301 as shown in FIG. 6. Restricting member 301 has aperture 302 in a prescribed shape. In a more preferable embodiment, an external force stopping member 304 is provided in aperture 302 of the restricting member. The upper face of the external force-stopping member is placed lower than the upper face of aperture 302 of the restriction member by a prescribed depth d. With this arrangement, sheet material P comes to be bent on application of external force as shown in FIG. 6. The difference in the bending behavior depending on the state of the sheet material can be detected. As an example, as shown in FIG. 6, external force applying member 20 is allowed to collide against a sheet material with a certain stroke by employing a compression coil spring or the like as driving source 303 (first collision); then sheet material P is bent by the collision (bending step); and the external force applying member collides against the external force stopping member (second collision) to apply external force. Through the above steps, the velocity (v1) of the external force applying member at the first collision is decreased by the sheet material. This decrease of the velocity depends on the properties of the sheet material such as the thickness and the material quality. Therefore, the velocity (v2) at the second collision reflects the information on the sheet material. Signal detecting means 3, which is provided onto the external force stopping member, gives outputs depending on v2 reflecting the sheet information. This embodiment is effective in detecting the information on bending rigidity and related properties of a sheet material: for example, the thickness, sheet material quality, density, tensile force of the sheet material, and further rigidity change by moisture of the sheet material.

<Anisotropy Impartment>

FIGS. 7 and 8 shows preferred shapes of the restricting member 301. In FIGS. 7 and 8, the mark "+" denotes the position where the external force is applied, and the mark "X" denotes the position where the sheet material is pushed by the sheet displacing means 4.

In FIG. 7, aperture 302 is made long in the sheet material feed direction: the breadth ($W_1$) perpendicular to the feed direction and the breadth ($W_2$) parallel to the feed direction are in the relation $W_1 < W_2$. The longitudinal direction thereof is made parallel to the feed direction. With such a constitution, anisotropic sheet materials such as cut paper sheets having lengthwise orientation and crosswise orientation can be effectively detected for the cut direction relative to sheet feed direction.

In FIG. 8, aperture 302 is circular ($W_1 = W_2$), having the center at around the external force application position. With this shape of the aperture, even an anisotropic sheet material is bent isotropically. Thereby, the properties of a sheet material can be effectively detected regardless of the orientation direction of the sheet material. Restricting member 301 has preferably a shape interfering less with the feed of the sheet material. In particular, aperture 302 has preferably a shape which does not cause collision of the front edge of the fed paper sheet against the wall of the aperture. For instance, aperture 302 is narrowed along the feed direction as shown in FIG. 7, or the member is curved to increase the interspace between the member and the sheet material along the feed direction. Otherwise the downstream side of the aperture may be cut out as shown in FIG. 9.

The dimensions of d, $W_1$, and $W_2$ are roughly in the ranges: 0.1 mm<d<2.0 mm, 5 mm<$W_1$<20 mm, and 5 mm<$W_2$<40 mm. Within these ranges, the information can be suitably detected on a recording medium such as plain paper, gloss paper, coated paper, regenerated paper and OHP paper.

A sheet sensor is preferably provided additionally to detect the state or position of the sheet material P (interaction of the sheet with external force applying means 2 or signal detecting means 3). The words "the state or position of the sheet material P (interaction of the sheet with external force applying means 2 or signal detecting means 3)" signifies a contacting state of the sheet material with the external force applying means 2 or signal detecting means 3; the position of the front edge of the sheet material; the state of passage of the sheet material; the pressure given by the sheet material to external force applying means 2 or signal detecting means 3; deformation of the sheet material; and so forth. The sheet sensor includes mechanical sensors and optical sensors for detecting contact or deformation, pressure sensors for detecting a pressure, and acceleration sensors for detecting vibration. Such a sheet sensor may be joined directly to external force applying means 2 or signal detecting means 3, or may be installed near external force applying means 2 or signal detecting means 3, and may be suitably designed for the sensor employed.

The feedback of the signal from the sheet sensor can optimize the control of external force applying means 2 or signal detecting means 3 for higher precision of sheet information detection. Further, the conditions such as the timing of beginning and stop of external force application, the strength of external force, and so forth can also be decided according to the signal from the sheet sensor. More information can be derived by utilizing the detection of the interaction of the sheet material with external force applying means 2 or signal detecting means 3 (pressure given by the sheet material, deformation of the sheet material, and so forth) in combination with the signal of impact application.

The aforementioned signal detecting means 3 can be comprised of an inorganic or organic material having a piezoelectric property, including specifically piezoelectric inorganic materials and piezoelectric organic materials such as PZT (lead titanate zirconate), PLZT, $BaTiO_3$, and PMN—PT(Pb $(Mg1/3Nb2/3)O_3$—$PbTiO_3$). With such a piezoelectric material, the external force is detected as a voltage signal.

The arrangement position of signal detecting means 3 is not limited insofar as the signal caused by the external force application can be detected. For instance, the signal detecting means may be placed in opposition to external force applying means 2 with interposition of sheet material P as shown in FIGS. 1 and 3, or at the same side as external force applying means 2. Signal detecting means 3 shown in the drawings supports the sheet displacing means 4 as the external force stopping member. Therefore, the signal detecting means 3 detects the external force received by the displacing means 4. With this arrangement, the absorption of the external force applied to the sheet material can be detected efficiently. The example of the latter (i.e., signal detecting means being placed at the side of external force applying means 2) includes the signal detecting means which detect vibration or positional change of an elastic member like a plate spring (not shown in the drawing) attached to the external force applying means; and signal detecting means which is attached to the external force applying means itself. With such an arrangement, rebound by the sheet material caused by the applied external force can be detected efficiently. Otherwise, two signal detecting means may be employed: one placed at the opposite side of external force applying means 2 with interposition of sheet material P and the other one at the same side as the external force applying means 2. With the arrangement of the signal detecting means attached to the external force applying means, a change of the external force applying means itself (e.g., resonance frequency, deformation, etc.) on contact with the sheet material can be detected. Further, residual vibration after stop of the external force application or attenuation thereof can be detected.

Figure 10:
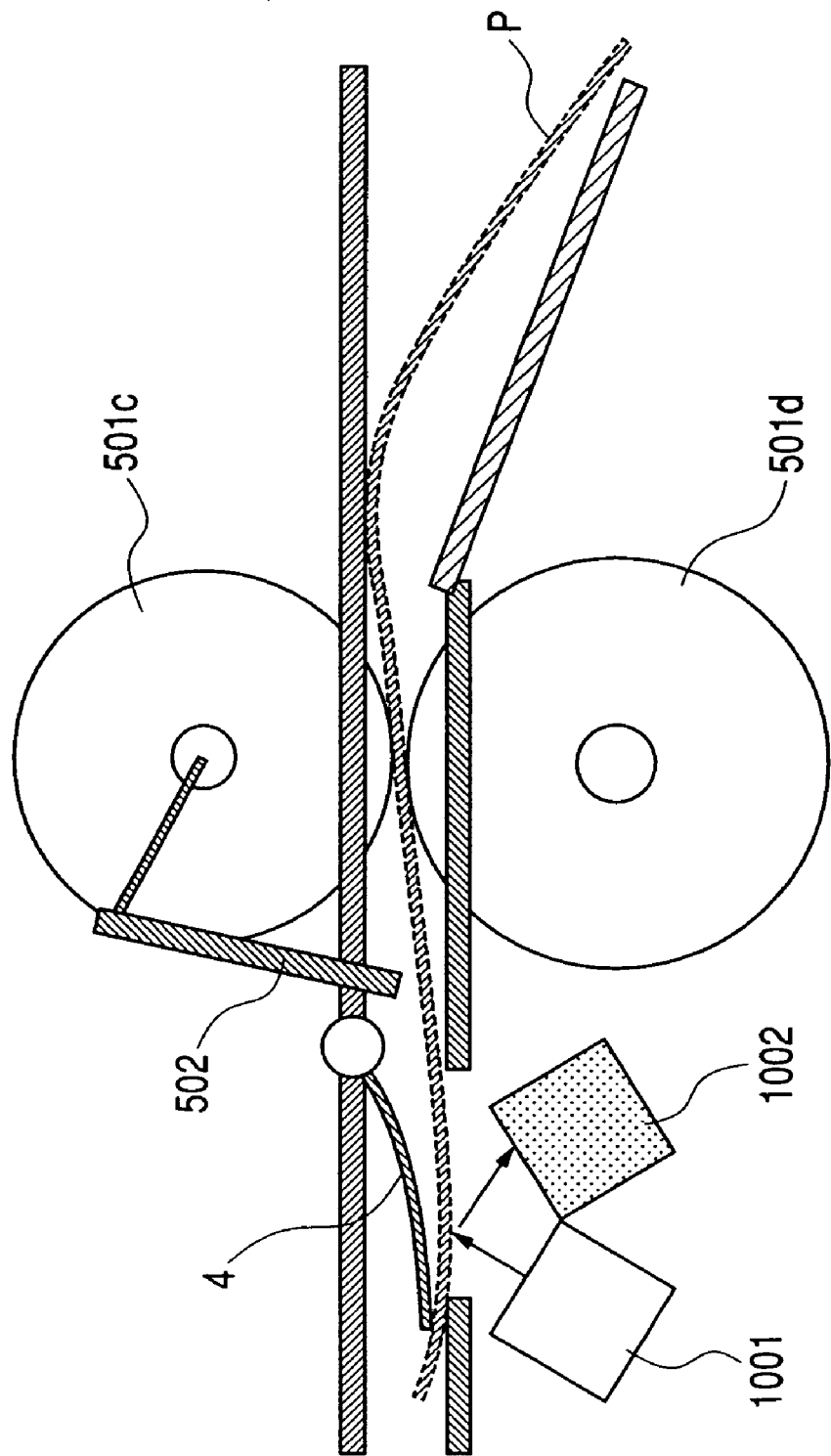
FIG. 10 is a sectional view showing an example of the structure of the sheet material information-detecting apparatus of the present invention.

The external force in the present invention includes waves. The wave includes ultrasonic waves, high-frequency waves, and optical waves. FIG. 10 illustrates an example of a sheet material information-detecting apparatus employing an optical wave. In FIG. 10, the numeral 1001 denotes a light source (external force applying means), and the numeral 1002 denotes a light-receiving element (signal detecting means). Light source 1001 may be omitted when a sufficient intensity of light can be received. Light-receiving element 1002 may be constituted of a single element of CCD, CMOS or the like, or an array of the elements. The information to be detected includes optical energy (wavelength), light quantity, distribution thereof, an image or the like, but is not limited provided that the information is detectable by the light-receiving element. Light source 1001 and light-receiving element 1002 may be placed on the same side of the sheet material as shown in FIG. 10, or may be placed in opposition with interposition of the sheet material.

Since the information detection is conducted after correction of oblique feed of the sheet material in the present invention, the information on the sheet material can be detected precisely even if the sheet material is anisotropic in the light reflectivity, surface roughness, or periodic structure thereof.

In detection of an image as the sheet material information, an interference phenomenon like moiré may occur depending on the periodic structure (e.g., fiber orientation structure of a paper sheet) of an observation object (sheet material) and arrangement of arrayed light-receiving elements, or the extent of the interference is varied by the oblique feed of the sheet material, causing an error in the information detection. The present invention lessens such adverse effect of the interference, enabling precise detection of the sheet material information.

The signal detecting means may be of one-dimensional arrangement or two-dimensional arrangement. With the latter two-dimensional arrangement, the breadth of the sheet material can be detected by employing a sensor assembly having a length equal to the breadth of the sheet material (e.g., a recording medium) or longer. Naturally, the breadth of the recording medium can be detected by plural sensor assemblies.

<Sheet Material Feeding Unit>

The embodiment of the present invention includes a sheet feeding unit incorporating the aforementioned sheet material information detecting-apparatus and a sheet feed driving assembly. FIG. 5 shows an example thereof. The sheet feed driving assembly is comprised of a pair of rollers 501*c* and 501*d* and a driving assembly not shown in the drawing. Oblique feed correcting means 502 comprises a shuttering member which is allowed to touch the front edge of the fed sheet to correct the oblique feed.

In another embodiment, the sheet material-treating apparatus of the present invention, as shown in FIG. 3, is comprised of a sheet material information-detecting apparatus (symbol B) and sheet material-treating assembly C for treating sheet material P based on the detection results of sheet material information-detecting apparatus B.

Sheet material-treating assembly C is exemplified by an image-forming assembly for image formation, a scanner assembly for reading an image, or like assemblies. The sheet material-treating apparatus includes copying machines, printers, facsimiles, scanners for image reading, and automatic document feeder.

In such an apparatus, CPU may be employed for conducting change of printing mode (e.g., adjustment of image formation conditions, adjustment of the feeding conditions such as a pressure given to a feeding rollers, stop of printing, stop of feed of a recording medium, generation of alarm signal, and so forth) based on the detection results of sheet material information-detecting apparatus B. The CPU may be installed in the inside of the sheet material-treating apparatus, or at the outside thereof. The CPU installed inside need not transmit or receive data signals to or from the outside.

The signal outputting apparatus may be comprised of external force applying means 2 for applying an external force to sheet material P; sheet displacing means 4 placed in opposition to the external force applying means 2 (with interposition of the sheet material) for controlling the position of sheet material P; and signal detecting means 3 for detecting a signal generated by the applied external force. The signal outputting apparatus of such a constitution is preferably connected to an external instrument which serves to acquire the sheet material information according to the output signal from the signal outputting assembly.

Next, the effects of embodiments of the present invention are explained below.

According to embodiment of the present invention, information on the sheet material can be obtained precisely even if the sheet material is anisotropic.

EXAMPLE

The present invention is explained in more detail by reference to an example.

In this Example, a paper type-detecting apparatus (a sheet material information-detecting apparatus) as shown in FIG. 3 is produced and is mounted on an electrophotographic apparatus (sheet material-treating apparatus).

In this apparatus, sheet feeding path A is formed by a pair of feed guide 10a and 10b, and feeding rollers (sheet feeding means) 1a, 1b, 1c and 1d are arranged along sheet feeding path A for feeding a recording paper sheet (sheet material). Of the rollers, upstream-side feeding rollers 1a and 1b serves also as oblique-feed correcting means. For oblique feed correction, the rotation of the rollers is stopped, and the nip between the rollers is narrowed to stop recording sheet P once for correction of oblique sheet feed. Then the nip is widened and feed of recording sheet is started by rotation of the rollers. The reference numeral 11 denotes a sheet material sensor placed near the roller 1a. This sensor detects the passage of the sheet material and displacement in the oblique feed correction.

External force applying means 2 and signal detecting means 3 are placed between rollers 1a and 1b and the rollers 1c and 1d.

At a portion of feed guide 10a, an aperture is formed, and bracket 12 is placed to cap the aperture. To bracket 12, are attached cushioning material 13, detecting sensor (signal detecting means) 3, and displacing member (sheet displacing means) 4 as shown in the drawing: cushioning material 13 supports detecting sensor 3, and the detecting sensor 3 supports displacing member 4 to allow displacing member 4 to protrude into the feed path. The dimension of the protrusion of displacing member 4 is one-fourth the breadth of feed path A (breadth at the position of displacing member 4) so that the recording sheet fed in the apparatus of this Example necessarily comes into contact with the displacing member 4 regardless of the type of the sheet (paper sheet or OHP sheet). Displacing member 4 is formed from a metal in a partial-cylindrical shape as shown in the drawing. The face of the displacing member for contact with recording paper sheet P is recessed at the upstream-side end and the downstream-side end from level of the aperture face of feed guide 10a on feed path A, and is allowed to protrude toward feed guide 10b at the middle portion thereof. The reference number 14 denotes a pushing-pressure controller.

As another embodiment, the contact face of the sheet displacing member is entirely recessed from the aperture face of feed guide 10a for feed guide A. In this embodiment, the sheet material is bent by application of an external force to allow the sheet material to come into contact with the contact face of the sheet displacing member, only when applying the external force thereto.

Detecting sensor 3 is comprised of PZT (lead titanate zirconate) as a piezoelectric material held between silver electrodes. The piezoelectric material has a length of 20 mm, a breadth of 5 mm, and thickness of 0.3 mm. Cushioning material 13 made of rubber is placed between bracket 12 and detecting sensor 3, whereby propagation of mechanical vibration from feed guide 10a to detecting sensor 3 is reduced to improve the detection accuracy. In FIG. 3, bracket 12 is fixed to feed guide 10a, but is not limited thereto. Bracket 12 may be connected to another bracket 211 on the side of feed guide 10b; bracket 12 and bracket 211 may be integrated into one body and connected to feed guide 10b; or bracket 12 may be connected to a portion other than feed guide 10a or 10b (e.g., casing, and frame) insofar as a suitable rigidity and fixing precision is achievable.

In this Example, paper presser 15 is provided to assist the contact of sheet material P with displacing member 4. Paper presser 15 is comprised of an elastic plate and a fixing member, and applies force by elasticity of the plate to the sheet material to push it to displacing member 4. Paper presser 15 has a mechanism (not shown in FIG. 3) which is moved by linking to the external force application and is withdrawn for waiting out of the sheet feed path. In this Example, displacing member 4 is brought into contact with the sheet material, but is not limited thereto and may be separated.

External force applying means 2 for applying an external force to recording paper sheet P is placed in opposition to displacing member 4. An aperture is provided in feed guide 10b and bracket 211 is placed in that portion. Roughly cylindrical guiding member 215 is attached to bracket 211, and rod 217 is placed to be movable horizontally in the guiding member 215. Pressing member (external force applying means) 20 is attached to the tip (tip at the recording sheet side) of rod 217. Stopper member 214 in a brim shape is provided at rod 217. Coil spring 210 in a compressed state is provided in the space between stopper member 214 and guide member 215. To bracket 211, motor 213 is attached, and to the output shaft of the motor, cam 212 is attached for pushing protrusion 218 attached to the end of rod 217. Incidentally, the reference numeral 216 denotes a pressure relief hole for mitigating damping by air in the guide member.

The aforementioned pressing member 20 applies external force to recording paper sheet P by collision at prescribed velocity with the aid of coil spring 210 and cam 212. When pressing member 20 is in a free state, the strength of the external force is decided by the product "mv" of the mass m of pressing member 20 and collision velocity v and interaction among pressing member 20, recording paper sheet P and the external force stopping member. For instance, for identification of the type of usual paper sheets, the strength of the external force ranges preferably from about 0.1 gm/s to about 10 gm/s. For one signal output, the external force is applied plural times preferably by changing the strength, whereby the information regarding the recording paper sheet can be detected with high precision.

In this Example, cam 212 is of two-step type having different steps for applying two different strengths of external forces by one rotation of motor 213. That is, higher cam 212 pushes projection 217 to move pressing member 20 upward, and releases pressing member 20 instantaneously to cause collision of pressing member 20 against recording paper sheet P by the spring force of coil spring 210, and thereafter lower cam 212 pushes projection 217 to move pressing member 20 upward, and releases pressing member 20 instantaneously to cause collision of pressing member 20 against recording paper sheet P by the spring force of coil spring 210. In this external force application, the strength of the external force applied to recording paper sheet is changed by using higher cam 212 and lower cam 212 by the difference of the compression distance of coil spring 210.

Another cam is attached also preferably to the driving shaft of cam 212 (i.e., rotation shaft of the motor) to displace the displacing member or an auxiliary displacing member by linking with external force application.

In this Example, displacing member 4 is placed in opposition to pressing member 20 to receive the external force.

In this Example, the data in the initial state without the sheet material is read by a processing apparatus before feed of the sheet material from the tray. This step of reading of the initial state may be omitted.

The operation in this Example is explained below.

Figure 4:
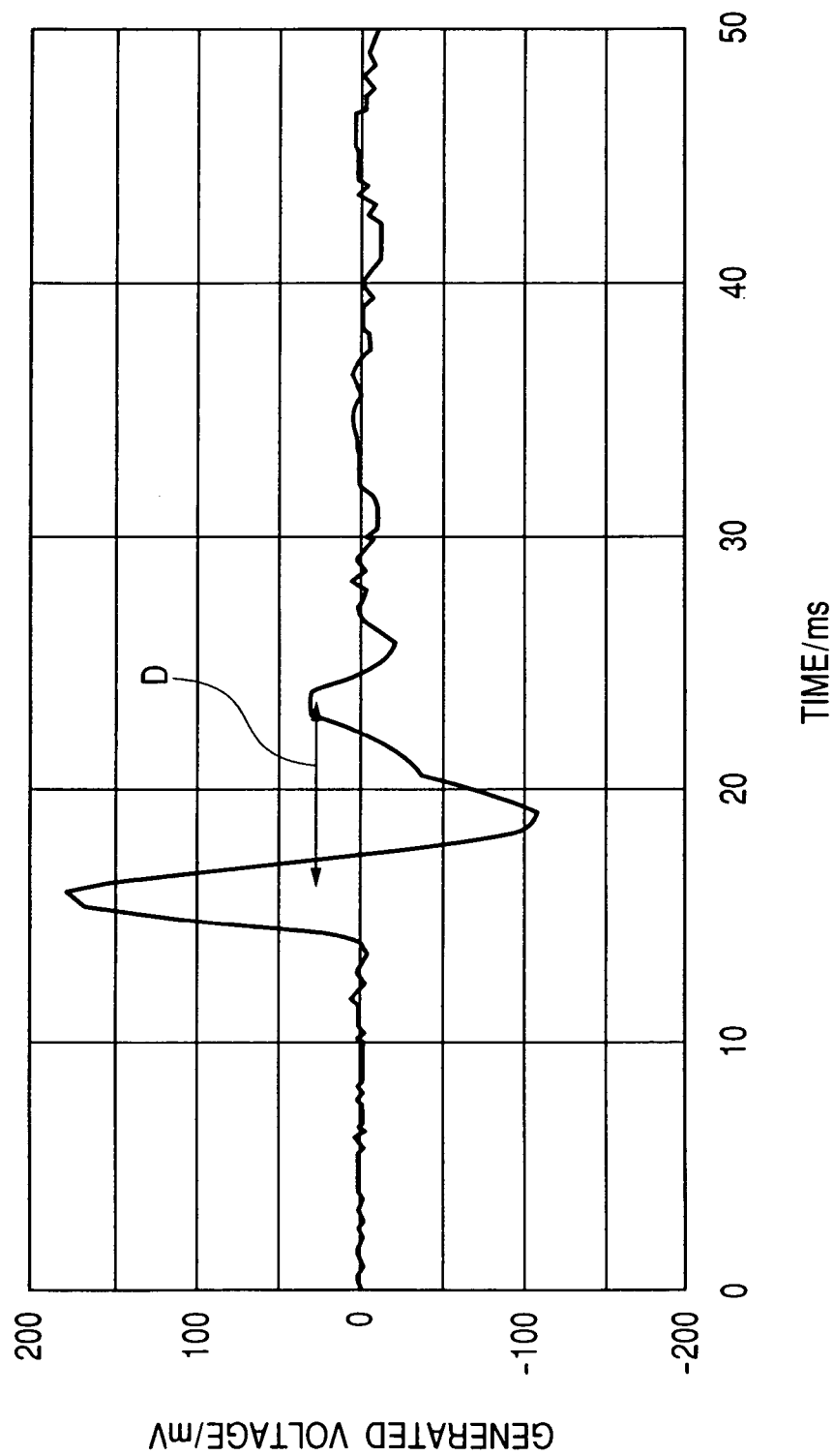
FIG. 4 is a waveform chart showing an example of the detected signal obtained by the signal detecting means.

Recording paper sheet P is fed by downstream-side feeding rollers 1c and 1d with the nip of upstream-side rollers 1a and 1b kept narrow. The recording paper sheet P is pushed against upstream-side rollers 1a and 1b to correct oblique feeding. Then, external force is applied by pressing member 20 to recording paper sheet P. The external force is transmitted through displacing member 4 to detecting sensor 3. Thereby, a signal as shown in FIG. 4 is outputted. This signal is obtained by detection of a plain paper sheet (Fuji Xerox Co.; ST(GAAA1896)). The information regarding surface roughness, friction, thickness distribution, and so forth can be extracted by analysis of voltage of the peaks, interval between peaks, and attenuation between peaks, and frequency analysis of the waveform of the signal.

According to this Example, information regarding a sheet material can be obtained even if the sheet material is anisotropic.

The invention claimed is:

1. A sheet material information-acquiring apparatus comprising:
    a sheet feeding unit for feeding an anisotropic sheet material;
    a correcting unit for correcting the position of the fed sheet material to bring the orientation direction of the constituting material of the sheet material to be in a prescribed direction relative to the feed direction of the sheet material;
    an external force applying unit for applying an external force to the sheet material in the corrected position, wherein the applied external force is a mechanical force; and
    an information-acquiring unit for acquiring information for changing a printing mode based on the stress caused by the applied external force in the sheet material.

2. The sheet material information-acquiring apparatus according to claim 1, further comprising a signal-detecting unit for detecting a signal from the sheet material, wherein the apparatus further comprises a sheet material sensor for sensing interaction of the external force applying unit and the signal-detecting unit with the sheet material.

3. The sheet material information-acquiring apparatus according to claim 2, wherein the sheet material sensor detects the state or position of the sheet material.

4. The sheet material information-acquiring apparatus according to claim 2, wherein the sheet information-acquiring unit acquires information by comparison of the result of the detection by the signal-detecting unit with data.

5. The sheet material information-acquiring apparatus according to claim 1, wherein the sheet information-acquiring unit acquires information on the sheet material by comparison of the result of detection by a signal-detecting unit with data for directions of the sheet material.

6. The sheet material information-acquiring apparatus according to claim 1, wherein the mechanical external force is one of plural impacts at different collision velocities.

7. The sheet material information-acquiring apparatus according to claim 6, wherein the external force is one of vibrations having different frequency components.

8. The sheet material information-acquiring apparatus according to claim 1, wherein a restricting member is provided for restricting the region of displacement of the sheet material on application of the external force.

9. The sheet material information-acquiring apparatus according to claim 1, further comprising a signal-detecting unit comprised of a material having a piezoelectric property.

10. A sheet-material treating apparatus, comprising the sheet material information-acquiring apparatus set forth in claim 1, and a sheet material-treating assembly for treating the sheet material by utilizing the information obtained by the sheet material information-acquiring apparatus.

11. A sheet material feeding unit comprising the sheet material information-acquiring apparatus set forth in claim 1, and a driving assembly for the sheet material feeding means.

12. A process for acquiring information on an anisotropic sheet material, comprising the steps of:
    collecting the position of a fed sheet material to bring the orientation direction of the constituting material of the sheet material to be in a prescribed direction relative to the feed direction of the sheet material;
    applying a mechanical external force to the sheet material in the corrected position; and
    acquiring information on the stress caused by the applied external force in the sheet material.

13. A sheet material-treating apparatus comprising:
    a sheet feeding unit for feeding an anisotropic sheet material;
    a correcting unit for correcting the position of the fed sheet material to bring the orientation direction of the constituting material of the sheet material to be in a prescribed direction relative to the feed direction of the sheet material;
    an external force applying unit for applying an external force to the sheet material in the corrected position, wherein the applied external force is a mechanical force;
    an information-acquiring unit for acquiring information on a stress caused by the applied external force in the sheet material; and
    a sheet material-treating unit for changing a printing mode according to the acquired information.

* * * * *

UNITED STATES PATENT AND TRADEMARK OFFICE
CERTIFICATE OF CORRECTION

PATENT NO.       : 7,422,208 B2                                                        Page 1 of 1
APPLICATION NO.  : 10/538267
DATED            : September 9, 2008
INVENTOR(S)      : Kawasaki et al.

It is certified that error appears in the above-identified patent and that said Letters Patent is hereby corrected as shown below:

ON THE COVER PAGE:
At Item (75), Inventors, "Takehiko Kawasaki, Tokyo (JP);" should read --Takehiko Kawasaki, Atsugi (JP);--.
At Item (57), Abstract, Line 10, "identify" should read --identifies--.

COLUMN 4:
Line 57, "is" should read --are--.

COLUMN 8:
Line 33, "shows" should read --show--.

COLUMN 9:
Line 53, "detect" should read --detects--.

COLUMN 11:
Line 37, "guide" should read --guides--.
Line 40, "serves" should read --serve--.

COLUMN 14:
Line 40, "collecting" should read --correcting--.

Signed and Sealed this

Tenth Day of February, 2009

JOHN DOLL
*Acting Director of the United States Patent and Trademark Office*